United States Patent [19]

Kinoshita et al.

[11] Patent Number: 5,442,949
[45] Date of Patent: Aug. 22, 1995

[54] THERMAL ANALYSER

[75] Inventors: Ryoichi Kinoshita, Tokyo; Yoshiyuki Takei, Iruma; Yoshizumi Takigawa, Iruma; Masahiro Furuno, Iruma, all of Japan

[73] Assignees: Seiko Instruments Inc., Tokyo; GL Science Inc., Saitama, both of Japan

[21] Appl. No.: 201,272

[22] Filed: Feb. 24, 1994

[30] Foreign Application Priority Data

Feb. 24, 1993 [JP] Japan .................................. 5-035848
Mar. 3, 1993 [JP] Japan .................................. 5-043059

[51] Int. Cl.$^6$ ........................ G01N 31/22; G01N 25/22
[52] U.S. Cl. .................................. 73/23.35; 73/23.41; 73/25.01; 422/68.1; 422/78
[58] Field of Search ................. 73/23.35, 23.41, 25.01; 422/68.1, 69, 78

[56] References Cited

U.S. PATENT DOCUMENTS

| | | | |
|---|---|---|---|
| 3,346,341 | 10/1967 | Sternberg | 73/23.35 |
| 3,847,546 | 11/1974 | Paul | 73/23.35 |
| 4,244,917 | 1/1981 | Woods et al. | 422/78 |
| 4,980,131 | 12/1990 | Meuzelaar et al. | 422/78 |
| 5,108,928 | 4/1992 | Menard et al. | 422/68.1 |
| 5,191,211 | 3/1993 | Gorman, Jr. | 73/23.35 |

FOREIGN PATENT DOCUMENTS

| | | | |
|---|---|---|---|
| 2192657 | 8/1987 | Japan | 73/23.35 |
| 2201156 | 8/1990 | Japan | 73/23.35 |
| 2203268 | 8/1990 | Japan | 73/23.35 |
| 1404933 | 6/1988 | U.S.S.R. | 73/23.35 |

*Primary Examiner*—Hezron E. Williams
*Assistant Examiner*—J. David Wiggins
*Attorney, Agent, or Firm*—Spensley Horn Jubas & Lubitz

[57] ABSTRACT

In a gas scavenging unit for gas chromatography analysis of gas generated in a thermal analyzer, the thermal analyser is equipped with a gas scavenging unit for scavenging gas generated in the thermal analyzer without usage of a carrier gas and no influence of a switching valve exists in the case of multi-stage sampling. For scavenging, there can be provided multiple sampling flow paths each have an aperture placed between the sample and the carrier gas outlet of the thermal analyzer, a flow regulator, a flow path switching valve, and a suction unit which is connected to the switching valve. The gas generated in the thermal analyzer is suctioned by the suction unit through a sampling flow path which is changed with the flow path switching valve. The appropriate volume of gas is scavenged to the GC analysis without any influence of the flow (rate) of the carrier gas even when the scavenging is done through switching to multiple scavengers.

7 Claims, 6 Drawing Sheets

THERMAL ANALYSER

BACKGROUND OF THE INVENTION

This invention relates to a thermal analyzer which includes a gas chromatograph for analyzing a gas generated from a sample placed in the thermal analyzer, and particularly a thermal analyzer equipped with a scavenging unit for scavenging the generated gas.

Prior art thermal analyzers which comprise a gas chromatograph (hereinafter called a GC) connected to a thermal analyzer are described as follows.

An exemplary prior art 1, Wiedemann, et al. (Thermal themal analysis Vol. 1, Academic, New York 1969, p. 229) discloses a connection of a thermal gravimetric analyzer (hereinafter called as TG) and a GC. Generated gas from the TG is introduced to an aggregate tube, which is called a "sample loop" with the aid of a carrier gas, and then the gas generated in the aggregate tube is introduced into the GC by switching the flow path via a sampling valve.

A prior art No. 2, J. H. Slaghuis, et al. (Thermochimica Act a, Vol. 175, 1991, p. 135), discloses that the generated gas from a TG is transmitted to a switching valve with the aid of a carrier gas, and then a sample which is obtained by sampling from a number of aggregate tubes into which the gas is fed is finally introduced into a GC.

According to a prior art No. 3, which is disclosed in the "SHIMAZ KAGAKU KIKAI News" Vol. 12, No. 10, 1971, p. 5, a gas is generated in a thermal analyzer and transmitted with the aid of a carrier gas and scavenged in a multiple number of aggregate tubes with a self-closing valve through a joint. Through another joint which is connected to each aggregate tube, the gas in the aggregate tube is introduced into a GC.

Acccording to a prior art No. 4, which is disclosed in the catalogue of Shimaz thermogranimetry gas chromatography mass spectrometer TGA-GCMS-QP1000EX, gas from a TG is transmitted with the aid of a carrier gas and scavenged into a trap (scavenger) via a cock, and then the gas which is in the trap is introduced into a CG by switching the cock.

According to a prior art No. 5, which is disclosed by YAMAHA et al. (Proc. 4th ICTA Conf. I. Buzas u. ed., Vol. 3 Heyden, London, 1975, p. 1029), gas from inside a differential thermal analyzer (hereinafter abbreviated as DTA) is introduced with the aid of a carrier gas from DTA into a scavenger, and then the gas is introduced into a GC by turning the scavenger off and sending it to the GC.

Generally speaking, the gas generated from the sample set in the thermal analyzer is generated due to a thermal decomposition and/or elimination reaction in relation to temperature rise, and such reaction itself is known to change according to measuring conditions (for example, programming rate, gas in the atmosphere, etc.) The flow rate of carrier gas used for the atmosphere control is also one of the measuring conditions. Accordingly, the flow rate of carrier gas should be given the same value for observing the difference etc. in reaction between samples.

The volume of the sample in case of analysis in a GC should be also appropriate. Accordingly, the volume of the gas to be generated in the thermal analyzer should also be appropriate in case of analyzing such gas which is to be introduced into the GC. In the prior art, sampling of such gas in analysis in a GC is made transmitting the gas with the aid of a carrier gas from the thermal analyzer.

In the prior art No. 1, No. 2, and No. 3, the gas is introduced into the aggregate tube with a predetermined capacity, and in the prior art No. 4 and No. 5, into a scavenger (absorbent, cold trap, or combination of both). Since the flow of carrier gas is constant, the sampling volume of the gas to be analyzed is determined on the basis of the capacity of the aggregate tube in case of sampling with an aggregate tube, or on the basis of the duration of time in case of sampling with a scavenger. Accordingly, in the transmitting method with carrier gas there exists a drawback that the range over which the best sampling in a GC can be done is narrow, as shown below.

In the use of an aggregate tube, the capacity for the gas to be sampled becomes very small if the speed of gas generation from the sample is very low, and sometimes a drawback exists that it can not be detected in a GC. On the contrary, in case that the capacity of the aggregate tube is increased for the purpose of increasing the gas generation for sampling above, the dead volume in injection to a GC increases, and therefore its isolation at the GC becomes worse in effect and becomes undetectable in practice.

In the use of the scavenger, the duration of time can be longer for scavenging gas in case of the slower gas generation. On the contrary, in case that the gas generation is very speedy, the sampling volume of the gas above becomes too large, and therefore it becomes not analyzable because of too much gas in the sampling hood in the analyzing column, which is another drawback. Moreover, there exists the following drawback in the prior art of transmitting sample gas with the aid of a carrier gas.

In the thermal decomposition reaction where gas generates, there exists often the case that the reaction mechanism becomes different in each stage of reaction, initiation, mature and ending. And in the case of plastic materials etc., a microelement of an addition agent, or a monomer which is not reacted yet, etc., may be present before the thermal decomposition. Accordingly, it is important to effect sampling and to analyze the gas at each stage of the reaction. In such a case above, a multiple number of aggregate tubes or scavengers is useful in sequential sampling at each stage of the reaction. As seen in the prior art No. 2 or No. 3, with the use of a switching valve or switching joint, the flow of the generation gas from the thermal analyzer is switched into specific aggregate tubes for sampling. In the case that the generation gas is transmitted in the prior art, the switching valve etc. for switching the flow of the gas above should be placed in between the thermal analyzer and the aggregate tubes, etc.

But there exists the following problem in case that a switching valve, etc. is placed in a flow path. It often occurs that the boiling point of the generation gas in thermal discomposition, etc. is higher than ordinary temperature. Therefore, the temperature of the flow path up to the aggregate tube is usually kept at, for example, 200° C., and the flow path is at a pressure higher than atmospheric pressure. The switching valve made of a metal such as stainless steel is usually the most appropriate since it is suitable for heat-proof and pressure-proof conditions. But, there is possibility that the generation gas above is trapped at the surface of the metal due to absorption or is exposed to a second order reaction. Valves made of inactivated glass in relation to the generation gas have a problem of pressure strength and valves made of plastic materials such as Teflon TM have problems of heat strength, of gas generation from such materials themselves, and/or of sample absorption.

This is to say, since sampling of the gas for analysis is made by using a carrier gas from a thermal analyzer in the prior art, there exists a difficulty in sampling an appropriate volume of gas in a GC for the measurement, and a problem that the materials of the switching valves, etc. affects to the measurement in case of multiple times of sampling of the gas above at multiple stages of reaction.

The object of this invention for the purpose of solving problems in prior art, is not to use a carrier gas for sampling of the gas above and therefore to carry out the sampling procedure with no relation to the flow of the carrier gas, and to obtain such constitution of a gas scavenging unit that a switching valve has no effect on the measurement even in the case of multiple stages of sampling.

SUMMARY OF THE INVENTION

For the purpose of solving the problems above, this invention has such a constitution that, in a scavenging unit which scavenges the gas to be generated from a sample set in the furnace of a thermal analyzer for GC analysis, the scavenging unit comprises a tube-type sampling flow path having apertures at its ends, with the aperture at one end being placed between the sample in the thermal analyzer and an outlet for carrier gas for atmosphere control, a scavenger connected to the aperture at the other end of the sampling flow path, and a suction unit connected to the scavenger.

Concerning scavenging of the gas at multiple stages, this invention has a constitution that the scavenging unit comprises a multiple number of sampling flow paths, a multiple number scavengers each connected to a respective sampling flow path, and a switching valve for switching the flow placed between each scavenger and the suction unit.

In such a scavenging unit that has the constitution above, the gas generated from the sample in the thermal analyzer is transmitted to the outlet of the carrier gas by means of the carrier gas.

DESCRIPTION OF THE PREFERRED EMBODIMENTS

Embodiments of this invention will be described with reference to the Figures.

Figure 1:
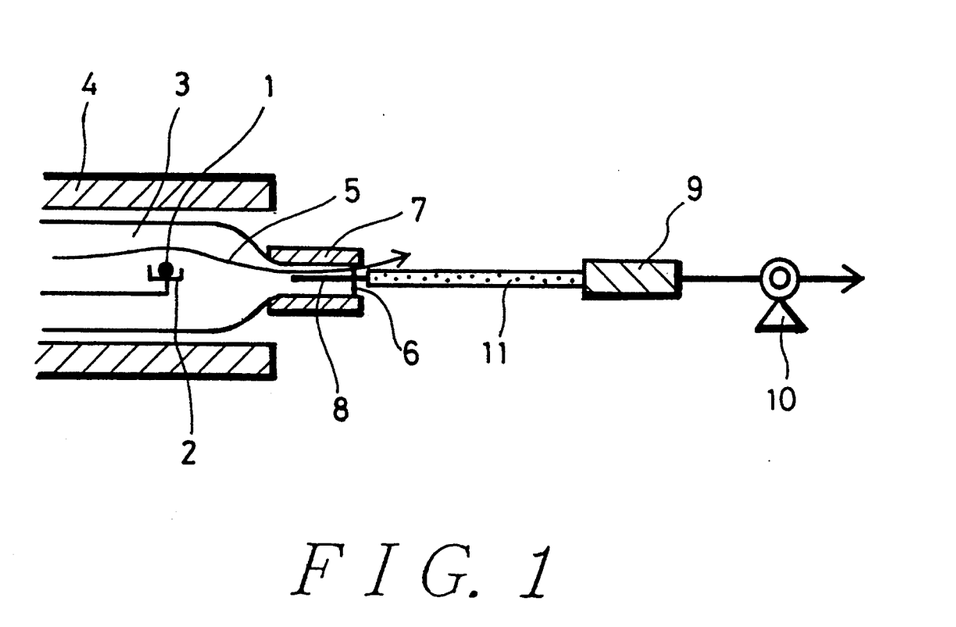
FIG. 1 is a cross-sectional view of the main parts of a first embodiment of this invention in which a tube-type sampling flow path having an aperture is placed between a sample and an outlet of a furnace tube.

FIG. 1 shows a first embodiment of the invention, in which a sample 1 is the object of a measurement in a thermal analyzer. Sample 1 is mounted on a sample holder 2 and sample 1 and holder 2 are enclosed in a furnace tube 3. Furnace tube 3 is enclosed in a furnace 4 which is operated for changing the temperature of sample 1 through the intermediary of furnace tube 3. Holder 2, furnace tube 3 and furnace 4 constitute the thermal analysis segment.

Line 5 identifies the flow of a carrier gas introduced for atmosphere control of the sample 1. The carrier gas entrains gas generated from sample 1 to the outside via an outlet 6 provided at the end of furnace tube 3. The inside diameter of outlet 6 is 3 mm. In the region of outlet 6, furnace tube 3 is enclosed by a heater 7 which heats the outlet portion of furnace tube 3, for preventing condensation of the gas which is conveyed with the carrier gas.

A tube-type sampling flow path 8 has an aperture placed between sample 1 and outlet 6. In this embodiment, flow path 8 is defined by a tube made of fused quartz with an inside diameter of 0.53 mm. A scavenger 9 is connected to the sampling flow path 8 and in this embodiment a glass tube is used for scavenger 9 as for flow path 8. Scavenger 9 is filled with a porous polymer absorbent (for example, Tenax) as a solid scavenging material. Scavenging material should only serve as an absorbent which absorbs the generated gas. Therefore, it can be a cold trap or combinations thereof.

A suction pump 10 is provided for suction of the gas which flows in sampling flow path 8. Gas in sampling flow path 8 which has its aperture located between sample 1 and outlet 6 is scavenged in scavenger 9 and is absorbed by the suction unit. The flow rate in sampling flow path 8 and in scavenger 9 can be adjustable by adjusting the suction power of the suction unit, therefore the sampling volume at the scavenger can be adjustable independently of the flow rate of carrier gas. Concerning sampling of the gas above in multiple stages, the gas generated as above is suctioned and scavenged into a sampling flow path which is connected to a selectively determined flow path by means of a switching valve placed in between the suction unit and a multiple number of scavengers. Since the switching valve is placed behind the scavengers, it does not affect the sampling of the gas at heater 7 for heating the gas to prevent condensation of the gas which passes through sampling flow path 8.

Thermal analysis segment 2-4 outputs a signal corresponding to a change of the sample material in relation to temperature. When the sample itself reacts in response to a temperature rise and generates gas, thermal analysis segment 2-4 outputs a signal which shows the decrease in weight in case of the thermogravity measuring equipment (TG), or a signal which indicates an endoergic or exoergic reaction. Such signal is accompanied with the reaction in case of the differential thermal analysis (DTA).

In the embodiment of FIG. 1, the furnace 4 is temperature-controlled by a controller which is not shown in the Figures, and heats sample 1. When a reaction occurs in sample 1 in accordance with this heating, the thermal analysis segment outputs the signal which signifies the change resulting from the reaction and gas generated due to the reaction is transmitted to outlet 6 by means of the carrier gas.

When the thermal analysis segment detects, say, a decrease in sample weight, in accordance with the operation of the suction pump 10, a part of the gas which is transmitted by means of the carrier gas is suctioned from sampling flow path 8, reaches scavenger 9 and then is absorbed by the scavenging materials. The volume of gas scavenged by scavenger 9 can be adjustable in relation to the power of, and the duration of absorption by, the suction pump.

In the measurement of plastics, for example, microelements of additives and/or monomers which do not react are sometimes absorbed slowly before thermal decomposition. In this case, the suction power should become stronger and suction should be continued while the absorption occurs. According to the procedure above, the gas generated through the absorption can be stored in scavenger 9. And then, when thermal decomposition of a primary element of the plastics is initiated to begin with and the speed of the gas generation is very fast, the suction power should become weaker and the duration of suction should be shortened. According to the adjustment as above, the appropriate volume of gas to be scavenged to the GC analysis can be obtained. Since the diameter of the outlet is 3 mm, and the inside diameter of the sampling flow path is 0.53 mm, there exists almost no influence in the suction on the flow rate of the carrier gas at the marginal space around the sample 1. Therefore, according to the method of sampling in this invention, the appropriate volume of sample to be scavenged can be attained independently of the flow rate of the carrier gas in the thermal analysis measurement.

Although the most inactive material is used for the sampling flow path in this invention, that is a tube made of fused quartz is used, a metal tube or plastic tube made of, say, Teflon TM can be used, when there exists no problem in reactivity with the gas above and/or in heat resistance.

In GC analysis, the gas is scavenged in the process of thermal analysis in the thermal analyzer or after the thermal analysis. After that, the scavenger is turned off and the heat absorption unit in the GC is turned on and is heated again. And then the gas in the scavenger is introduced into the GC column by means of the carrier gas in the GC.

Figure 2:
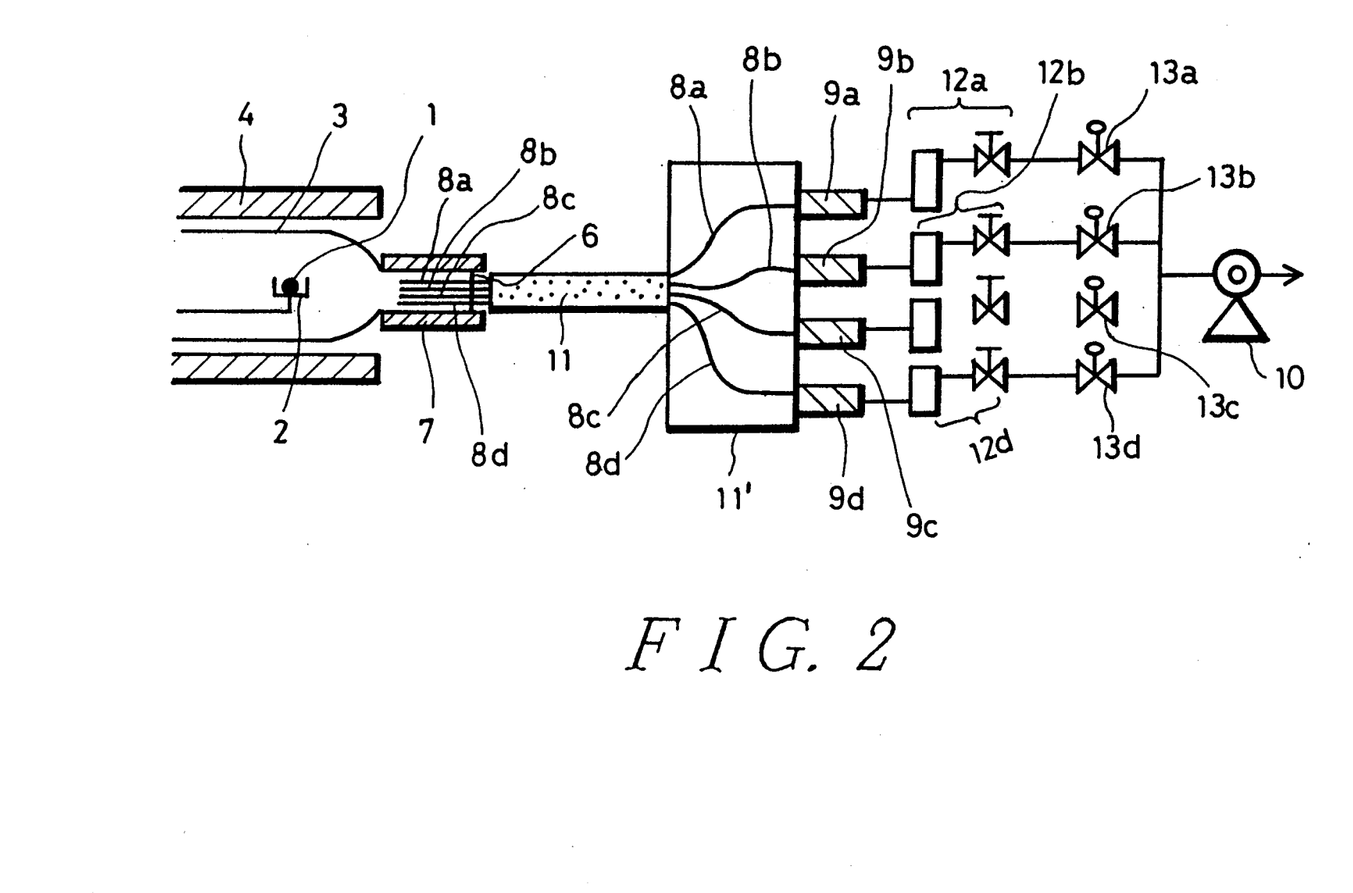
FIG. 2 is a cross-sectional view of the main parts of a second embodiment of this invention in which a plurality of tube-type sampling flow paths are provided.

FIG. 2 shows a second embodiment of the invention. Elements 1 through 7 are as same as in the embodiment of FIG. 1. Elements 8a through 8d are annular sampling flow paths the aperture of each of which is placed in between the sample 1 and the outlet 6, and these are constituted by four fused quartz tubes each with an inside diameter of 0.53 mm. Elements 9a through 9d are scavengers, each of which is connected to a sampling flow path 8a through 8d, respectively, and Tenax as the scavenging material is filled in the glass tubes of elements 9a to 9d, as in the embodiment of FIG. 1. The sampling flow paths 8a through 8d are kept warm by heater 11 and heating cover 11'. Suction pump 10 suctions gas through the sampling flow paths 8a through 8d. Flow regulators 12a through 12d are each constituted by flow meter coupled with a needle valve. Magnetic valves 13a through 13d are located between suction pump 10 and scavengers 9a through 9d.

In this embodiment, there exists four pieces of the sampling flow paths for the gas. For example, once magnetic valve 13a becomes open, the gas is scavenged into scavenger 9a through sampling flow path 8a, and once magnetic valve 13b becomes open, the gas is scavenged into scavenger 9b through sampling flow path 8b. Therefore, it becomes possible to scavenge the gas generated separately at the each stage of the thermal analysis into scavengers 9a through 9d by operation of magnetic valves 13a through 13d. In this embodiment, the suction force of the suction pump can be adjustable at an optional level, by control of the suction flow rate in sampling flow path 8a by the associated flow regulator 12a or by control of the duration of the suction by opening or closing of the magnetic valve 13a. That is, the gas generated at each stage in thermal analyzing measurement can be scavenged up to the appropriate level of volume in relation to the speed of the gas generation by opening and closing of the magnetic valves 13. Since there exist switching valves by which four pieces of the sampling flow paths are changed over behind the scavenger for scavenging of the gas, it is clear that no trap or second order reaction of the switching valves themselve has any effect at the time of the gas scavenging.

Figure 3:
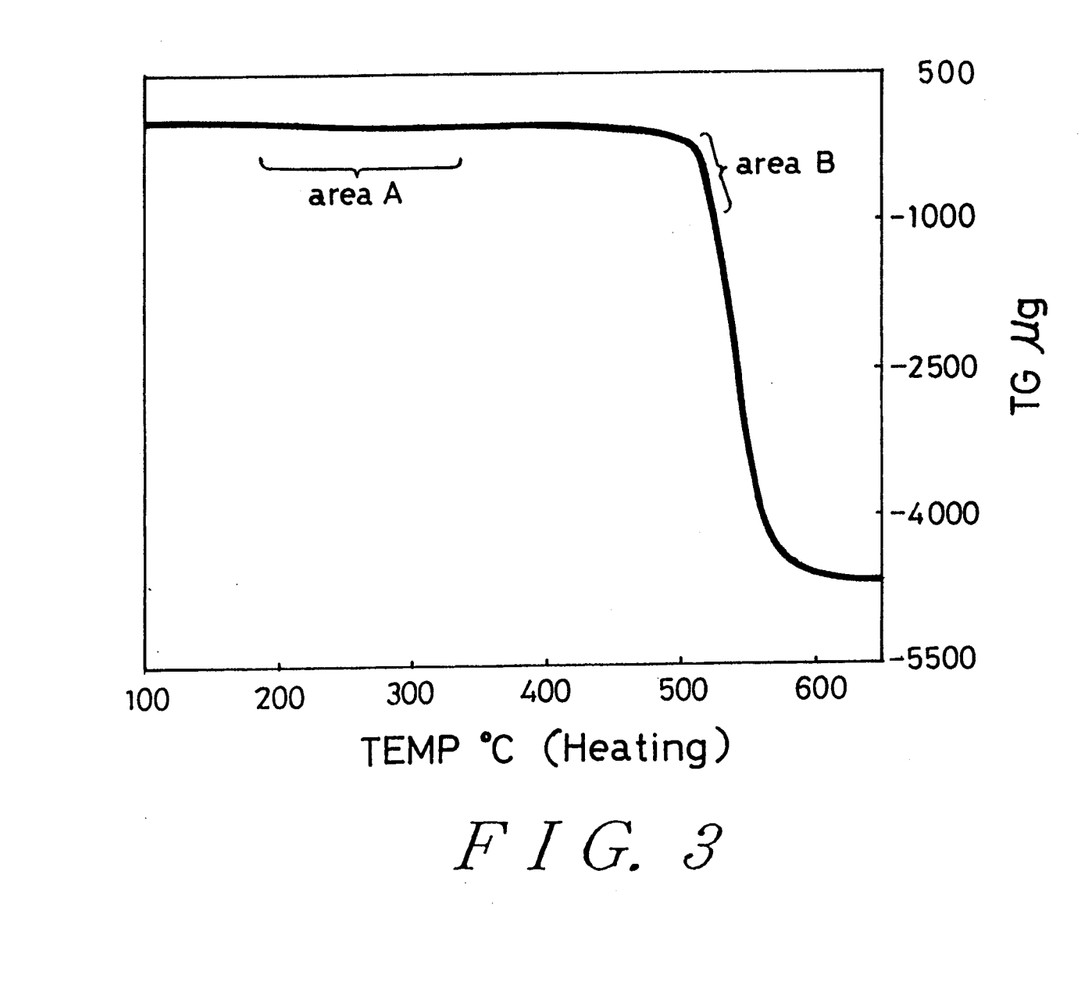
FIG. 3 is a graph showing data relating to a plastic sample measurement with apparatus for thermogravimetry (TG).
Figure 4:
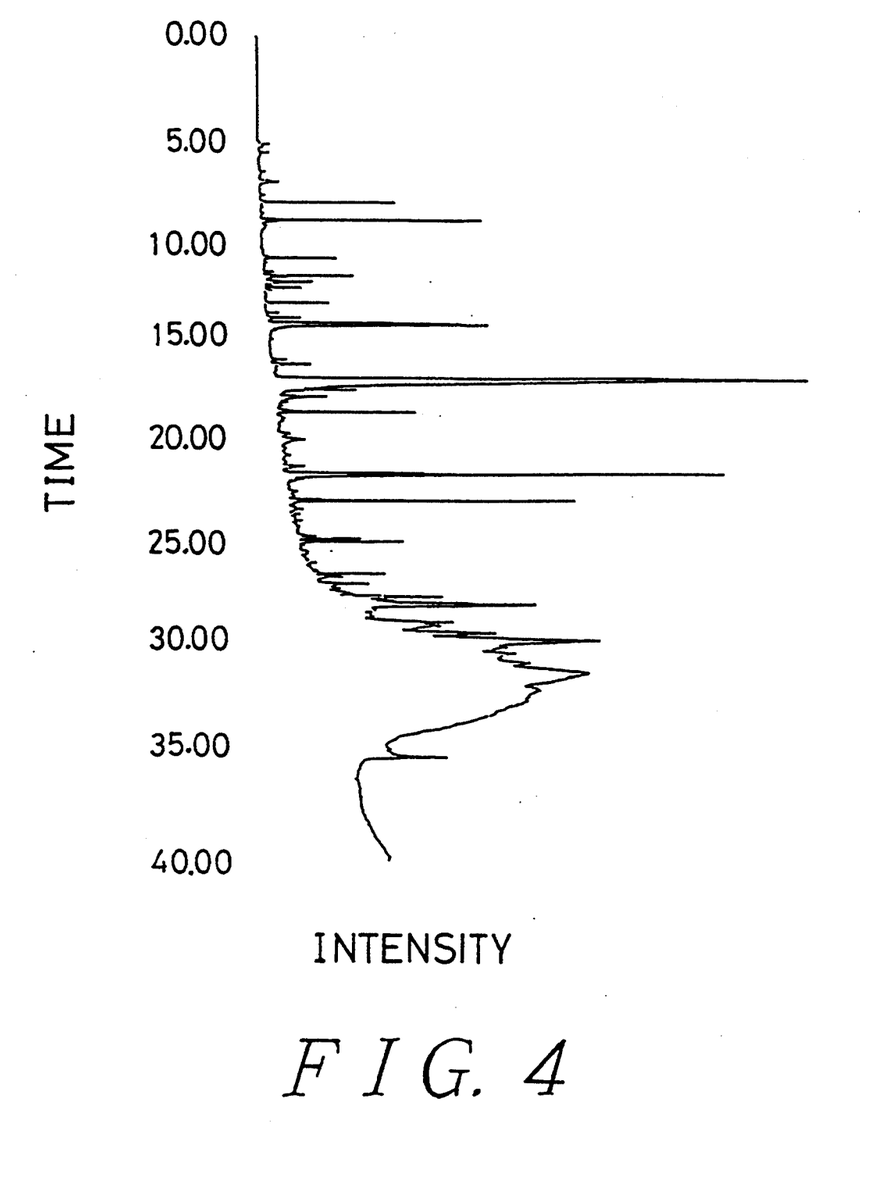
FIG. 4 is a graph of a chromatogram resulting from the analysis by a GC after the scavenging of the gas generated by the gas scavenging unit in an embodiment of the present invention in the area A shown in FIG. 3.
Figure 5:
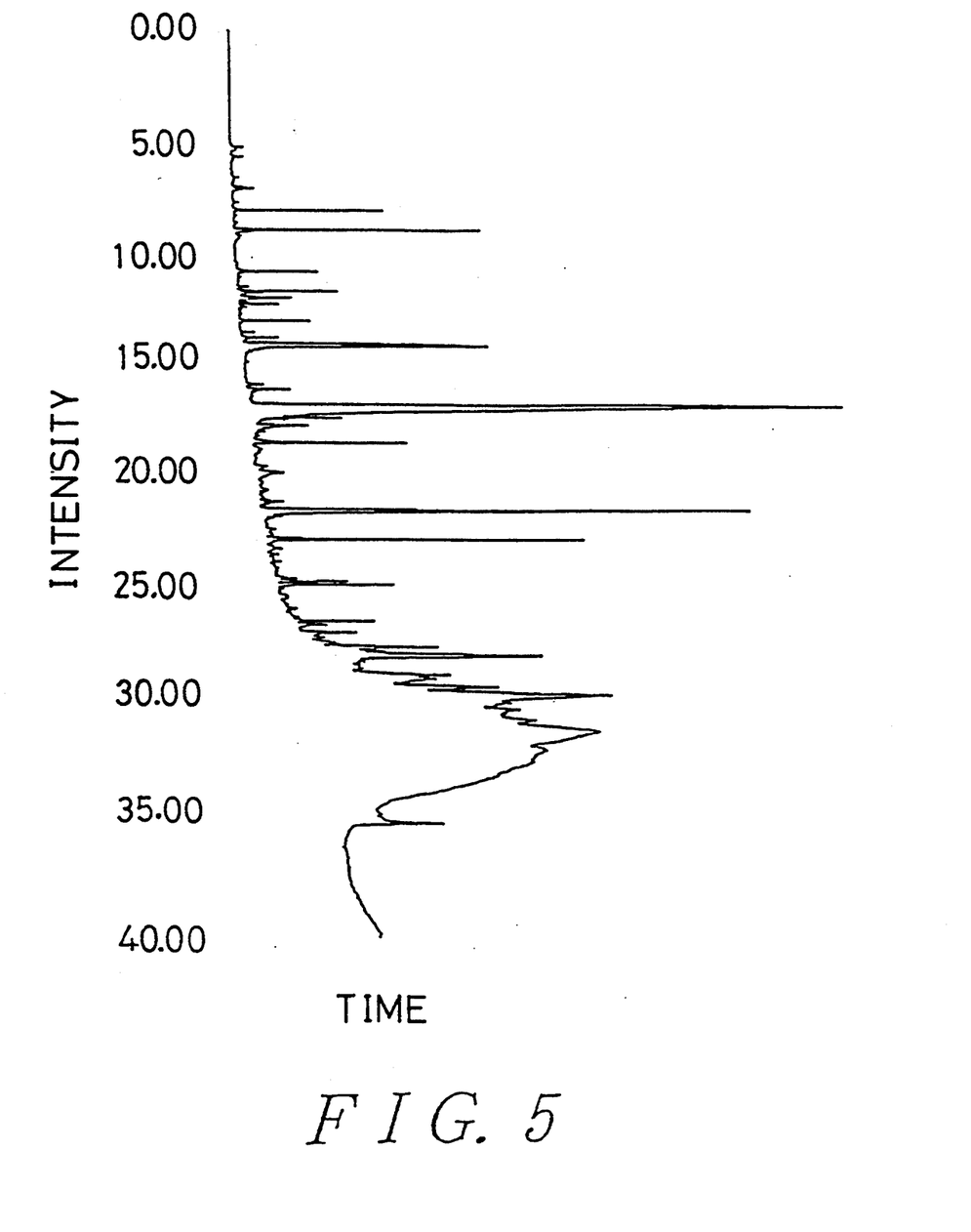
FIG. 5 is a graph of a chromatogram resulting from the analysis by a GC after the scavenging of the gas generated by the gas scavenging unit in an embodiment of the present invention in the area B shown in FIG. 3.

FIG. 3 shows the relevant data of plastic samples measured by apparatus for thermogravimetry. In this measurement, 200 ml/min of gaseous nitrogen is supplied as the carrier gas. FIG. 4 and FIG. 5 show chromatograms analyzed by a GC of the gas generated which was scavenged by the gas scavenging unit according to the invention, of which the scavenging specification is a sampling flow rate of 30 ml/min. for each of the area A and the area B, in both at 12 sec. of the sampling hour.

The area A is where a microelement of monomer which has not reacted is in the course of desorption, and where the decrease in the weight of the sample is slow and the generation speed of gas is also low, on the TG curve. On the contrary, in the area B where thermal decomposition is occurring, the decrease in the weight is fast and the generation speed of gas is also fast. But proper chromatograms were obtained in both cases in this embodiment as shown in FIG. 4 and FIG. 5, because the gas generated was scavenged appropriately through the change in the scavenging duration (the duration of suction) during sampling in relation to the generation speed of gas generation.

Although a multiple number of magnetic valves is used in order to change over the multiple number of flow paths, a multi-way access cock which performs a switching function between multiple flow paths can also be used. And although the flow regulator is disclosed above as having a flow meter and a needle valve, only a needle valve or mass-flow meter can be also used, so long as they can control the flow rate.

In the embodiment of FIG. 2, flow regulators 12a through 12d can be eliminated as well, or only one sampling flow path can also be used instead the plural number used in the illustrated embodiment. And moreover is it clear too, that the scavenging of an appropriate volume of gas can be realized by establishing a variable sampling flow rate by having the flow rate changed through the opening and closing of the magnetic valves 13a through 13d where only one flow regulator is provided instead of the four flow regulators 12a through 12d shown in FIG. 2.

Figure 6:
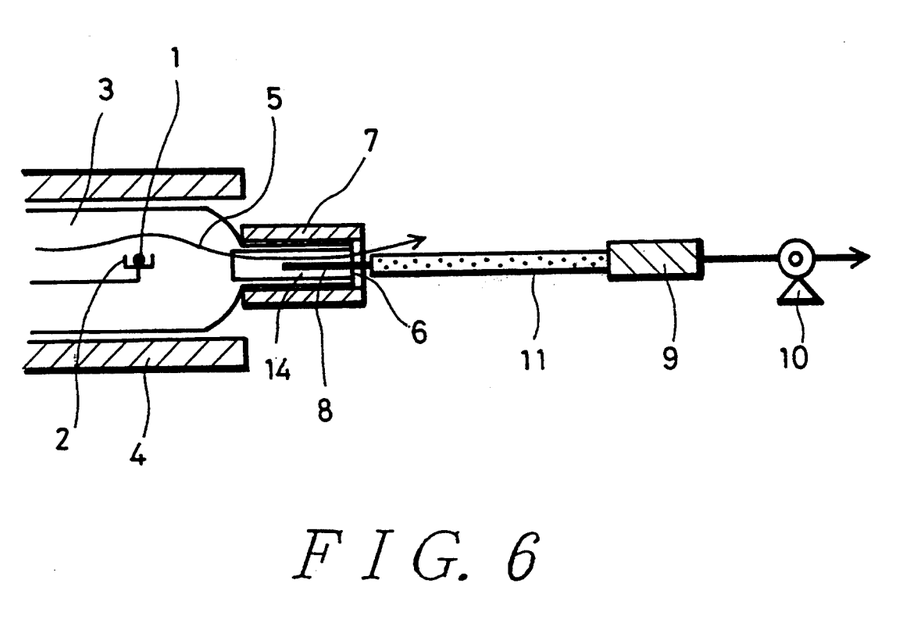
FIG. 6 is a cross-section view of a third embodiment of this invention provided with a detachable trapping tube.

FIG. 6 shows another embodiment of this invention, where elements 1 through 8 are the same as in the embodiment of FIG. 1 and a detachable trapping tube 14 is provided for selectively trapping high boiling elements.

Trapping tube 14 in this embodiment has an outside diameter of 3 mm, is made of fused quartz and is inserted at the outlet end of furnace tube 3. Trapping tube 14 is heated by heater 7 at the outlet end of furnace tube 3. Heater 7 is controlled by the temperature controller 5 which is not shown in the Figures.

Miscellaneous decomposition products are emitted by sample 1, by thermal decomposition, and there sometimes exist high boiling elements with boiling points of 300° C. or higher. But once a high boiling point element 10 having a boiling point of 300° C. or higher is introduced into a GC, degradation or jamming can occur in the CG column or contamination can also occur inside of the detector. In order to avoid these situations, it is necessary to scavenge element(s) which are left after high boiling elements only are eliminated from all the heat decomposition elements. And once high boiling point element gasses are generated and suctioned into the sampling flow path, or paths, jamming in the sampling flow paths can sometimes happen and in this case scavenging of gas can not be realized in the scavenger.

When the temperature of the trapping tube 14 is kept at, say, 300° C., high boiling element(s) with boiling points of 300° C. or more in the gas which is carried with the carrier gas condense and are trapped around the surface of the trapping tube 14 before those elements can be suctioned into the sampling flow path 8, and suction of those elements into the sampling flow path can be avoided. And the repetition of heat analysis measurement invites accumulation of high boiling point elements around the surface of the trapping tube, which can be absorbed from the surface of the trapping tube at the time of the next measurement. But in this embodiment, since the trapping tube 14 is detachable, it can be detached and washed, or replaced with a new one. Therefore such a problem as mentioned above does not occur at the next measurement in this invention.

In a scavenging unit for scavenging the gas generated from the sample disposed in the thermal analyzer for the purpose of gas chromatography analysis, this invention, as explained as above, has a constitution comprising a tube-type sampling flow path having an aperture which is placed in between the sample in the thermal analyzer and the outlet of carrier gas for environment control, a scavenger which is connected to another end of the sampling flow path, and a suction unit which is connected to the scavenger. Therefore, this invention has the good effect that an appropriate volume of the gas to the GC analysis can be obtained without any influence by the flow volume of the carrier gas, which is a measurement condition in a thermal analyzer.

Moreover, since this invention has a constitution comprising a multiple number of sampling flow paths each having an aperture placed in between the sample in the thermal analyzer and the outlet of carrier gas for environment control, a multiple number of scavengers each connected to the another end of a respective sampling flow path, and a flow path switching valve which is placed in between the scavenger and the suction unit which is connected to the scavenger, this invention has the good effect that there exists no influence of trapping, second-order reactions, etc. at the flow switching valve even when scavenging of the gas is done through the change over of multiple scavengers by the time of scavenging of the gas generated from the sample in the thermal analyzer.

When a detachable trapping tube, in the neighborhood of the aperture of the sampling flow path, and a temperature control unit for the control of the trapping tube are provided in embodiments of the invnetion, the invention has another good effect, when multiple consecutive measurements are executed, that the jamming at the sampling flow path is avoided and therefore that no influence on the GC analysis exists, because scavenging can be performed after the selective elimination of high boiling elements.

What is claimed is:

1. In a thermal analyzer in which a gas which is generated from a sample placed at a sample location in a furnace is analyzed by gas chromatography, the thermal analyzer having an inlet for receiving a carrier gas which conveys the generated gas, in combination with a scavenging unit for scavenging the generated gas, the improvement, wherein said thermal analyzer has a gas outlet for exhausting carrier gas from said thermal analyzer and said scavenging unit comprises:

means defining at least one tube-type sampling flow path having an inlet disposed between the sample location and said gas outlet for receiving at least a fractional part of the generated gas conveyed through said thermal analyzer, said flow path further having an outlet communicating with said flow path inlet, where the remaining fraction of generated gas is conveyed through said thermal analyzer outside of said tube-type sampling flow path;

at least one scavenger connected to said flow path outlet for scavenging generated gas received at said flow path inlet and flowing along said flow path; and a suction unit connected to said a scavenger for drawing generated gas into said flow path via said flow path inlet and then into said scavenger.

2. A thermal analyser as claimed in the claim 1 wherein:

said means defining at least one tube-type sampling flow path define a plurality of flow paths each having a respective inlet disposed between said sample location and said gas outlet for receiving at least a part of the generated gas and a respective outlet communicating with the respective flow path inlet;

said at least one scavenger comprises a plurality of scavengers each connected to a respective flow path outlet; and said scavenging unit further comprises switching valve means connected between each said scavenger and said suction unit;

wherein gas which is generated at different times in said thermal analyzer can be scavenged in different ones of said scavengers by operation of said switching valve means to connect different ones of said scavengers to said suction unit.

3. A thermal analyser as claimed in the claim 2, further comprising a flow regulator connected between said scavengers and said suction unit, wherein said flow regulator is controllable for adjusting the rate of flow of generated gas through each said sampling flow path.

4. A thermal analyser claimed in the claim 2, wherein: said switching valve means comprise a plurality of switching valves each connected to a respective scavenger; and said thermal analyzer further comprises a plurality of flow regulators each connected between a respective switching valve and said suction unit, wherein each said flow regulator is controllable for adjusting the rate of flow of generated gas through a respective sampling flow path.

5. A thermal analyser as claimed in the claim 1, further comprising a flow regulator connected between said scavenger and said suction unit, wherein said flow regulator is controllable for adjusting the rate of flow of generated gas through said sampling flow path.

6. A thermal analyser as claimed in the claim 1, further comprising a quickly detachable trapping tube which is placed at said thermal analyzer gas outlet for selectively eliminating only high boiling point elements from the generated gas suctioned into said sampling flow path, and a temperature controlling unit located for maintaining said trapping tube at a temperature below the boiling point of each high boiling point element.

7. A thermal analyzer comprising:
- a furnace for heating a sample to cause gas to be generated from the sample for analysis, said furnace having a sample location for holding the sample;
- a furnace tube disposed in said furnace and surrounding said sample location, said furnace tube having an inlet for receiving a carrier gas which conveys the generated gas and a gas outlet for exhausting carrier gas;
- means defining at least one tube-type sampling flow path having an inlet disposed between said sample location and said gas outlet for receiving at least a fractional part of the generated gas conveyed through said thermal analyzer, said flow path further having an outlet communicating with said flow path inlet inlet, where the remaining fraction of generated gas is conveyed through said thermal analyzer outside of said tube-type sampling flow path;
- at least one scavenger connected to said flow path outlet for scavenging generated gas received at said flow path inlet and flowing along said flow path; and
- a suction unit connected to said a scavenger for drawing generated gas into said flow path via said flow path inlet and then into said scavenger.

* * * * *